US009513245B2

(12) United States Patent
Sakai et al.

(10) Patent No.: US 9,513,245 B2
(45) Date of Patent: Dec. 6, 2016

(54) CAPACITIVE HUMIDITY SENSOR

(75) Inventors: Minekazu Sakai, Kariya (JP); Naohisa Niimi, Kariya (JP)

(73) Assignee: DENSO CORPORATION, Kariya (JP)

( * ) Notice: Subject to any disclaimer, the term of this patent is extended or adjusted under 35 U.S.C. 154(b) by 477 days.

(21) Appl. No.: 14/116,149

(22) PCT Filed: May 22, 2012

(86) PCT No.: PCT/JP2012/003329
§ 371 (c)(1),
(2), (4) Date: Nov. 7, 2013

(87) PCT Pub. No.: WO2012/160806
PCT Pub. Date: Nov. 29, 2012

(65) Prior Publication Data
US 2014/0139241 A1 May 22, 2014

(30) Foreign Application Priority Data
May 25, 2011 (JP) .................................. 2011-117195

(51) Int. Cl.
*G01R 27/26* (2006.01)
*G01N 27/22* (2006.01)
*G01N 27/04* (2006.01)

(52) U.S. Cl.
CPC .......... *G01N 27/223* (2013.01); *G01N 27/225* (2013.01); *G01N 27/048* (2013.01)

(58) Field of Classification Search
CPC .. G01N 27/221; G01N 27/121; G01N 27/223; G01N 27/225; G01N 19/10
See application file for complete search history.

(56) References Cited

U.S. PATENT DOCUMENTS 5,801,307 A * 9/1998 Netzer .............. B32B 17/10036
73/170.17
7,471,093 B2 * 12/2008 Arisaka ................ G01N 27/225
324/664

(Continued)

FOREIGN PATENT DOCUMENTS

JP       07-030015 A     1/1995

OTHER PUBLICATIONS

International Search Report of the International Searching Authority mailed Aug. 7, 2012 for the corresponding international application No. PCT/JP2012/003329 (with English translation).

(Continued)

*Primary Examiner* — Minh N Tang
(74) *Attorney, Agent, or Firm* — Posz Law Group, PLC

(57) ABSTRACT

A humidity sensor includes a detection device with a capacitance changing with humidity at a first ratio and a reference device with a capacitance changing with humidity at a second ratio smaller than the first ratio. The detection device has detection electrodes facing each other with a first gap and a detection humidity-sensitive film covering the detection electrodes. The reference device has reference electrodes facing each other with a second gap and a reference humidity-sensitive film covering the reference electrodes. The detection humidity-sensitive film and the reference humidity-sensitive film are made from the same material and have the same thickness. The detection electrodes and the reference electrodes are made from the same material and have the same width and thickness. The second ratio peaks when the second gap is equal to a predetermined value. The second gap is smaller than the first gap and the predetermined value.

8 Claims, 5 Drawing Sheets

(56) References Cited

U.S. PATENT DOCUMENTS

| | | |
|---|---|---|
| 2002/0141136 A1 | 10/2002 | Toyoda et al. |
| 2003/0094045 A1 | 5/2003 | Hamamoto et al. |
| 2003/0179805 A1 | 9/2003 | Hamamoto et al. |
| 2005/0188764 A1 | 9/2005 | Itakura et al. |
| 2006/0096370 A1 | 5/2006 | Isogai et al. |
| 2007/0210807 A1 | 9/2007 | Arisaka |

OTHER PUBLICATIONS

Written Opinion of the International Searching Authority mailed Aug. 7, 2012 for the corresponding international application No. PCT/JP2012/003329 (with English translation).

Office Action mailed Jan. 14, 2014 for the corresponding JP application No. 2011-117195 (with English translation).

\* cited by examiner

CAPACITIVE HUMIDITY SENSOR

CROSS REFERENCE TO RELATED APPLICATION

This application is a U.S. national stage application of PCT/JP2012/003329 filed on May 22, 2012, and is based on Japanese Patent Application No. 2011-117195 filed on May 25, 2011, the contents of which are incorporated herein by reference.

TECHNICAL FIELD

The present disclosure relates to a capacitive humidity sensor in which a detection capacitive device and a reference capacitive device are formed on a common substrate. A capacitance of the detection capacitive device changes with a change in ambient humidity. A ratio of a change in capacitance of the reference capacitive device to a change in the humidity is different from that of the detection capacitive device. In particular, the present disclosure relates to a capacitive humidity sensor in which a detection capacitive device and a reference capacitive device are formed on the same surface of a substrate, and each of the detection capacitive device and the reference capacitive device has a humidity-sensitive film.

BACKGROUND ART

For example, a patent document 1 discloses a capacitive humidity sensor in which a detection capacitive device and a reference capacitive device are formed on a common substrate. A capacitance of the detection capacitive device changes with a change in ambient humidity. A ratio of a change in capacitance of the reference capacitive device to a change in the humidity (hereinafter sometimes simply referred to as the ratio) is different from that of the detection capacitive device.

In the patent document 1, the detection capacitive device (a first sensor device) has a pair of detection electrodes (comb-shaped electrodes) and a detection humidity-sensitive film (a humidity-sensitive film). The detection electrodes are located to face each other on the same surface of the substrate, and a detection humidity-sensitive film (a humidity-sensitive film) covers the detection electrodes. A relative permittivity of the detection humidity-sensitive film changes when the detection humidity-sensitive film absorbs water. The reference capacitive device (a second sensor device) has a pair of reference electrodes (comb-shaped electrodes) and a reference humidity-sensitive film (a humidity-sensitive film). The reference electrodes are located to face each other on the surface (the above same surface) where the detection electrodes are located, and the reference humidity-sensitive film covers the reference electrodes. A relative permittivity of the reference humidity-sensitive film changes when the reference humidity-sensitive film absorbs water. According to the patent document 1, the reference humidity-sensitive film and the detection humidity-sensitive film are integrated as a single humidity-sensitive film, and this humidity-sensitive film collectively covers the detection electrodes and the reference electrodes that are located on the same surface of the substrate.

Thus, the reference electrodes are protected by the humidity-sensitive film (a reference humidity-sensitive film). Therefore, compared to a structure in which the reference capacitive device has no humidity-sensitive film, deterioration of the reference capacitive device is reduced so that a variation in the capacitance of the reference capacitive device can be reduced even in hot and humid conditions.

PRIOR ART

Patent Document

Patent Document 1: JP-A-2006-133191

In the capacitive humidity sensor, a difference in capacitance between the detection capacitive device the reference capacitive device is converted to a voltage by a known CV conversion circuit, and a relative humidity in the atmosphere is detected based on the voltage. As a difference in the ratio between the detection capacitive device and the reference capacitive device shown in FIG. 2 of the patent document 1 is larger, a change in the difference in capacitance with respect to a change in humidity becomes larger. That is, the sensitivity of the capacitive humidity sensor is improved.

In the patent document 1, since the humidity-sensitive film (a reference humidity-sensitive film) is also provided to the reference capacitive device, the capacitance of the reference capacitive device also changes with the relative humidity. Therefore, the sensitivity of the capacitive humidity sensor is low compared to the structure in which the reference capacitive device has no humidity-sensitive film (FIG. 5 of the patent document 1). Therefore, in view of the sensitivity, it is preferable that the ratio of the reference capacitive device, i.e., C2/C1, which is a ratio of a capacitance C2 at a relative humidity of 100% to a capacitance C1 at a relative humidity of 0%, be as small (close to 1) as possible. The sensitivity may be improved by increasing the ratio of the detection capacitive device (a capacitance ratio C2/C1). However, in this case, since the size of the detection capacitive device is increased, the size of the capacitive humidity sensor is increased accordingly.

It is noted that the electrode gap and the ratio (a capacitance ratio C2/C1) has a relationship such that the ratio peaks when the electrode gap is equal to a predetermined value. The ratio increases with an increase in the electrode gap until the electrode gap reaches the predetermined value. The ratio decreases with an increase in the electrode gap, when the electrode gap exceeds the predetermined value. The details are explained in embodiments of the invention.

The relative permittivity of the humidity-sensitive film itself does not change with humidity. However, depending on the amount of absorbed water, the relative permittivity of the whole including the water changes. Therefore, as the influence of the humidity-sensitive film on the capacitance formed in the electrode gap is larger, the ratio (a capacitance ratio C2/C1) of the change in capacitance to the change in humidity becomes larger. The capacitance of each capacitive device (the detection capacitive device and the reference capacitive device) depends on an overlap capacitance and a fringe capacitance in the pair of opposing electrodes (the detection electrodes and the reference electrodes). The overlap capacitance is formed between overlap surfaces. The fringe capacitance is formed between lower surfaces facing the substrate and between upper surfaces opposite to the lower surfaces. Out of these capacitance components, in particular, the fringe capacitance formed between the upper surfaces is generally much influenced by the humidity-sensitive film when the electrode thickness (the height of the overlap surface) is greater than the electrode width (the length of the upper surface) because the humidity-sensitive film located between the upper surfaces is larger. The reason why the ratio increases with the increase in the electrode gap until the electrode gap reaches the predetermined value can be considered that as the electrode gap is smaller, the influence of the overlap capacitance is larger (in other words, the influence of the humidity-sensitive film is smaller) and that as the electrode gap is larger, the influence of the fringe capacitance is larger (in other words, the influence of the humidity-sensitive film is larger).

In FIG. 1 of the patent document 1, the electrode gap of the reference capacitive device is larger than the electrode gap of the detection capacitive device. Therefore, in view of the above relationship between the electrode gap and the ratio (a capacitance ratio C2/C1), to improve the sensitivity by increasing the difference between the ratio of the detection capacitive device and the ratio of the reference capacitive device, the electrode gap of the reference capacitive device needs to be set in such a manner that the electrode gap of the reference capacitive device is larger than a value at which the ratio (a capacitance ratio C2/C1) of the reference capacitive device peaks and that the difference between the ratio of the reference capacitive device and the ratio of the detection capacitive device is large. For this reason, it is difficult to reduce the size of the reference capacitive device and therefore the size of the capacitive humidity sensor.

SUMMARY OF THE INVENTION

In view of the above, it is an object of the present disclosure to improve the sensitivity and to reduce the size of a capacitive humidity sensor in which a detection capacitive device and a reference capacitive device are formed on the same surface of a substrate, and the reference capacitive device also has a humidity-sensitive film.

According to an aspect of the present disclosure, a capacitive humidity sensor includes a substrate, a detection capacitive device formed on the substrate, and a reference capacitive device formed on the substrate. A capacitance of the detection capacitive device changes with a change in ambient humidity at a first ratio, and a capacitance of the reference capacitive device changes with the change in ambient humidity at a second ratio smaller than the first ratio. The detection capacitive device includes a pair of detection electrodes and a detection humidity-sensitive film that covers the detection electrodes. The detection electrodes face each other on a predetermined mounting surface of the substrate and are spaced from each other by a first gap. A relative permittivity of the detection humidity-sensitive film changes with absorption of water. The reference capacitive device includes a pair of reference electrodes and a reference humidity-sensitive film that covers the reference electrodes. The reference electrodes face each other on the mounting surface of the substrate and are spaced from each other by a second gap. A relative permittivity of the reference humidity-sensitive film changes with absorption of water. The detection humidity-sensitive film and the reference humidity-sensitive film are made from the same material and have the same thickness. The detection electrodes and the reference electrodes are made from the same material and have the same width and thickness. The first ratio is a ratio of the capacitance of the detection capacitive device at a relative humidity of 100% to the capacitance of the detection capacitive device at a relative humidity of 0%. The second ratio is a ratio of the capacitance of the reference capacitive device at a relative humidity of 100% to the capacitance of the reference capacitive device at a relative humidity of 0%. The first ratio reaches its peak, when the first gap is equal to a predetermined value. The second ratio reaches its peak, when the second gap is equal to the predetermined value. The second gap is smaller than the first gap and the predetermined value.

Since each electrode gap is set so that the ratio of the detection capacitive device becomes larger than the ratio of the reference capacitive device, the sensitivity of the capacitive humidity sensor can be improved. Further, since the electrode gap of the reference capacitive device is set smaller than a value at which the ratio of the reference capacitive device reaches its peak, the size of the reference capacitive device and therefore the size of the capacitive humidity sensor can be reduced.

Thus, it is possible to improve the sensitivity and to reduce the size of the capacitive humidity sensor in which the detection capacitive device and the reference capacitive device are formed on the same surface of the substrate, and the reference capacitive device also has the humidity-sensitive film.

BRIEF DESCRIPTION OF THE DRAWINGS

The above and other objects, features and advantages of the present disclosure will become more apparent from the following detailed description made with reference to the accompanying drawings. In the drawings.

EMBODIMENTS OF THE INVENTION

Figure 1:
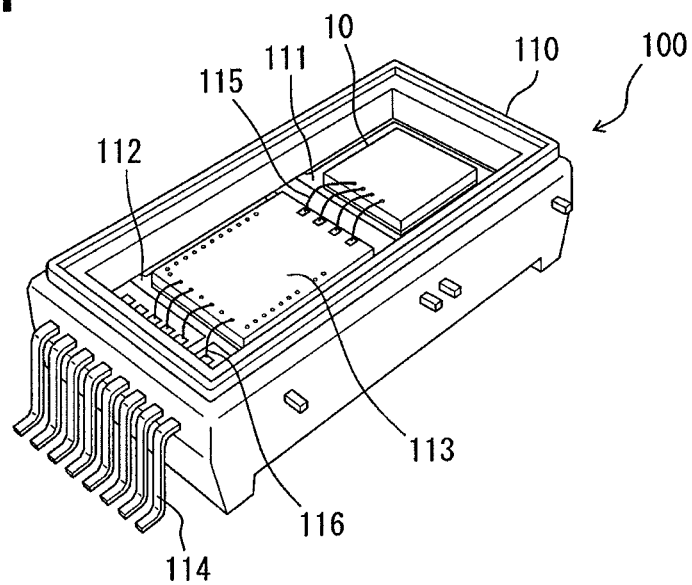
FIG. 1 is a diagram illustrating a perspective view of a humidity detection apparatus including a capacitive humidity sensor according to an embodiment, in which a protection gel is omitted for the sake of convenience.

Embodiments of the present disclosure are described below with reference to the drawings in which like reference numerals depict like elements. In a plan view of FIG. 2, a humidity-sensitive film and a dam section are hatched to indicate areas where they are formed.

FIG. 1 shows a humidity detection apparatus 100 including a capacitive humidity sensor 10 according to an embodiment. The humidity detection apparatus 100 includes a casing 110 made from synthetic resin and shaped like a rectangular tube with a bottom, lead frame islands 111 and 112 fixed to an inner surface of the bottom of the casing 110, a capacitive humidity sensor 10 mounted on the island 111, a circuit chip 113 mounted on the island 112, and a lead 114 having a first end located inside the casing 110 and a second end located outside the casing 110.

The capacitive humidity sensor 10 and the circuit chip 113 are electrically connected together by a bonding wire 115. The circuit chip 113 and the lead 114 are electrically connected together by a bonding wire 116. Although not shown in FIG. 1, the bonding wire 115, the bonding wire 116, and their connection portions (pads) are covered with protection gel (a protection gel 60 shown in FIG. 3).

In this way, according to the embodiment, the capacitive humidity sensor 10 is a separate chip from the circuit chip 113 having a CV conversion circuit.

Next, a structure of the capacitive humidity sensor 10 is described.

Figure 2:
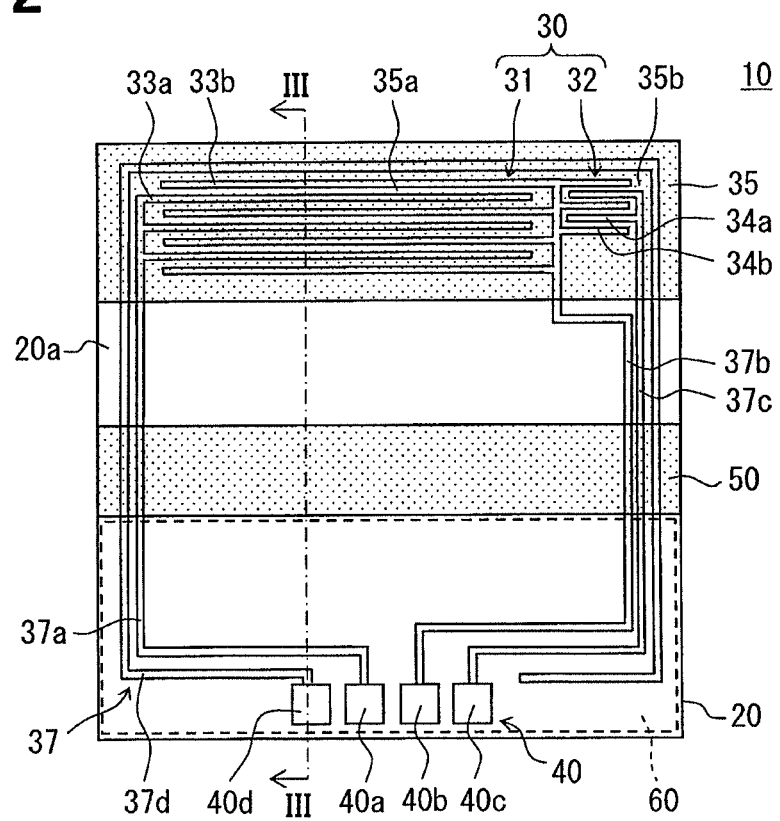
FIG. 2 is a diagram illustrating a plan view of the capacitive humidity sensor according to the embodiment, in which a detection electrode, a reference electrode, a wire connected to a pad are indicated by a solid line, and the protection gel is indicated by a broken line for the sake of convenience.
Figure 3:
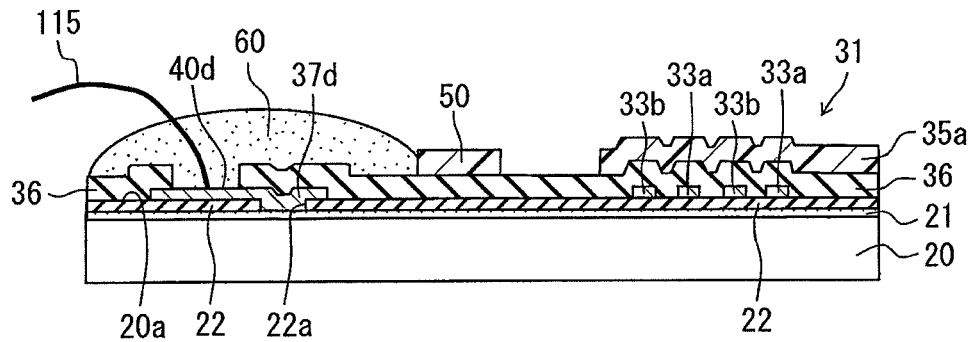
FIG. 3 is a diagram illustrating a cross-sectional view taken along line III-III in FIG. 2, in which the number of electrodes is reduced for the sake of convenience, and showing a condition where the pad connected to a bonding wire is covered with the protection gel.

The capacitive humidity sensor 10 is a so-called sensor chip. As shown in FIGS. 2 and 3, a humidity detection section 30, a pad 40 as an external connection terminal, and a dam section 50 for limiting movement of a protection gel 60 are formed on a common substrate 20 (a semiconductor chip). The protection gel 60 is arranged on the substrate 20 in such a manner that the pad 40 and a connection portion at which the bonding wire 115 is connected to the pad 40 are covered with the protection gel 60 under a condition where the bonding wire 115 is connected to the pad 40.

According to the embodiment, the substrate 20 is a silicon substrate. As shown in FIG. 3, an impurity diffusion layer 21 is formed in a surface portion of the whole of a first surface of the substrate 20. Specifically, the diffusion layer 21 is a p-conductivity type diffusion layer. An insulating layer 22 is formed on the diffusion layer 21, and a contact hole 22a is formed in part of the insulating layer 22. According to the embodiment, the insulating layer 22 includes a silicon oxide layer and a BPSG layer that are layered on top of each other in this order from the substrate 20 side.

The humidity detection section 30, the pad 40, and the dam section 50 are formed on the insulating layer 22. According to the embodiment, the substrate 20 and the insulating layer 22 are collectively referred to as a substrate, and an opposite side of the insulating layer 22 from the substrate 20 is referred to as a first surface 20a of the substrate 20.

Figure 4:
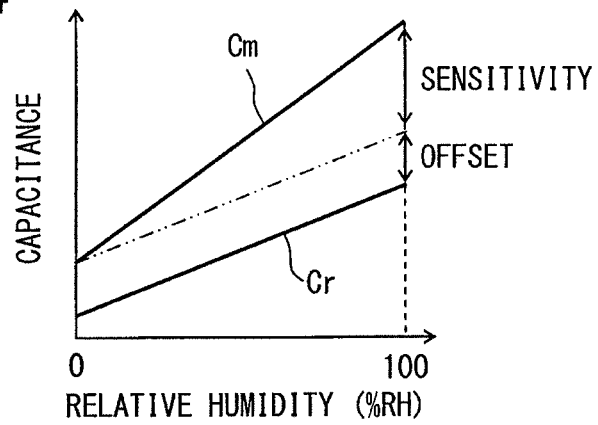
FIG. 4 is a diagram illustrating a relationship between a relative humidity and a capacitance.

The humidity detection section 30 includes a detection capacitive device 31 and a reference capacitive device 32. A capacitance of each of the detection capacitive device 31 and the reference capacitive device 32 changes with a change in relative humidity, and a ratio of a change in capacitance to a change in humidity is different between the detection capacitive device 31 and the reference capacitive device 32. As shown in FIG. 4, a capacitance at a relative humidity of 0%, i.e., an initial capacitance of the detection capacitive device 31 (a capacitance Cm) is larger than that of the reference capacitive device 32 (a capacitance Cr). Further, the ratio of a change in capacitance to a change in humidity of the detection capacitive device 31 is larger than that of the reference capacitive device 32.

As shown in FIG. 4, a difference in the initial capacitance between the capacitive devices 31 and 32 is an offset. A sensitivity of the capacitive humidity sensor 10 is a change in a value, which is obtained by subtracting the offset from a capacitance difference, with respect to a change in humidity. Therefore, the sensitivity can be improved by increasing a difference in the ratio of the change in capacitance to the change in humidity between the capacitive devices 31 and 32.

The detection capacitive device 31 has a pair of detection electrodes 33a, 33b that face each other on the first surface 20a of the substrate 20. The reference capacitive device 32 has a pair of reference electrodes 34a, 34b that face each other on the first surface 20a of the substrate 20 at a different position from where the detection electrodes 33a, 33b are located.

The shapes of the detection electrodes 33a, 33b and the reference electrodes 34a, 34b are not limited. According to the embodiment, the detection electrodes 33a, 33b have a comb-shape and are alternately arranged. Due to the comb-shape, while the layout area of the detection electrodes 33a, 33b is reduced, the overlapping area of the detection electrodes 33a, 33b is increased. Thus, a change in a capacitance between the detection electrodes 33a, 33b with respect to a change in ambient humidity is increased, so that the sensitivity of the capacitive humidity sensor 10 can be increased. Likewise, the reference electrodes 34a, 34b have a comb-shape and are alternately arranged.

Figure 5:
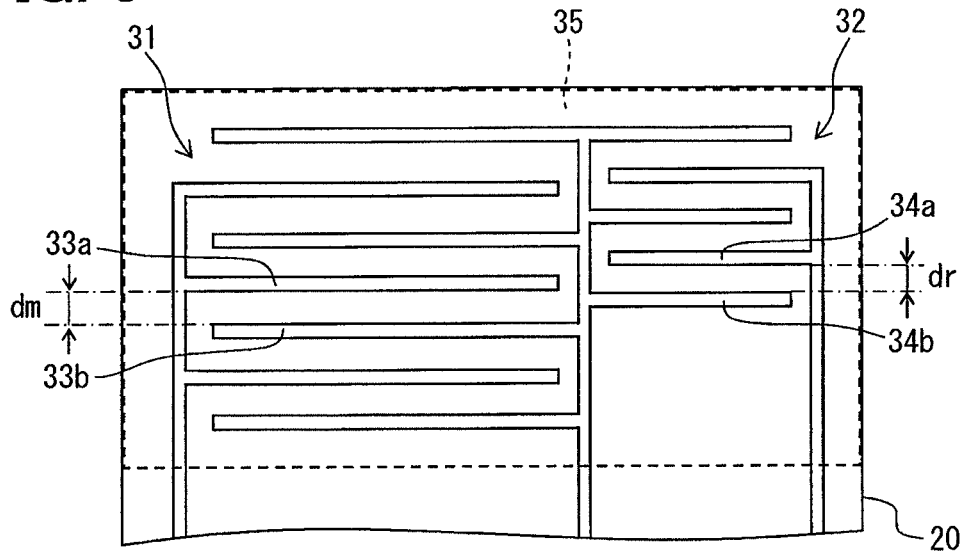
FIG. 5 is a diagram illustrating an enlarged view of FIG. 2 around a detection capacitive device and a reference capacitive device, in which part of the wire connected to the pad is omitted for the sake of convenience, the detection electrode and the reference electrode are indicated by a solid line like in FIG. 2, and a humidity-sensitive film is indicated by a broken line.

Further, as shown in FIG. 5, the length of the overlapping portion of the detection electrodes 33a, 33b is longer than that of the reference electrodes 34a, 34b. Further, the number of teeth of the comb-shape of the detection electrodes 33a, 33b is larger than that of the reference electrodes 34a, 34b. Therefore, the overlapping area of the detection electrodes 33a, 33b is larger than that of the reference electrodes 34a, 34b. The initial capacitance of the detection capacitive device 31 is larger than that of the reference capacitive device 32.

A distance between the detection electrodes 33a, 33b, i.e., an electrode gap dm of the detection capacitive device 31 and a distance between the reference electrodes 34a, 34b, i.e., an electrode gap dr of the reference capacitive device 32 are set to satisfy a predetermined condition. The setting condition is a main feature of the embodiment. The details are described later.

The detection electrodes 33a, 33b and the reference electrodes 34a, 34b are made from the same material and have the same width and thickness. Specifically, wiring material capable of being corroded by water, such as aluminum, is deposited on the first surface 20a of the substrate 20 to an almost uniform thickness by vapor deposition, sputtering, or the like. Then, in a photolithography process, a comb-shape having teeth with almost the same width is patterned. According to the embodiment, the detection electrodes 33a, 33b, the reference electrodes 34a, 34b, and the pad 40 are made from aluminum.

As shown in FIG. 3, a protection film 36 is formed on the detection electrodes 33a, 33b and the reference electrodes 34a, 34b. A humidity-sensitive film 35 is formed on the protection film 36. The humidity-sensitive film 35 includes a reference humidity-sensitive film 35b that covers the reference electrodes 34a, 34b.

The protection film 36 protects the detection electrodes 33a, 33b and the reference electrodes 34a, 34b from corrosion due to water. According to the embodiment, the protection film 36 is a silicon nitride layer formed by a plasma CVD method. The protection film 36 is formed on the first surface 20a of the substrate 20 to cover not only the detection electrodes 33a, 33b and the reference electrodes 34a, 34b but also portions except the pad 40.

A detection humidity-sensitive film 35a is formed on the protection film 36 to cover the detection electrodes 33a, 33b and a portion between the detection electrodes 33a, 33b. Further, the reference humidity-sensitive film 35b is formed to cover the reference electrodes 34a, 34b and a portion between the reference electrodes 34a, 34b. The humidity-sensitive films 35a and 35b are made from the same material and have almost the same thickness.

According to the embodiment, the detection humidity-sensitive film 35a for covering the detection electrodes 33a and 33b and the reference humidity-sensitive film 35b for covering the reference electrodes 34a and 34b are integrated as a single humidity-sensitive film 35. According to the embodiment, the humidity-sensitive film 35 is made from polyimide-type material. After precursor (polyamide) is coated on the first surface 20a of the substrate 20 by a spin coating method or a printing method, a heating and hardening treatment (an imidization treatment) is performed so that the humidity-sensitive film 35 can be formed to an almost uniform thickness.

The electrodes 33a, 33b, 34a, and 34b of the capacitive devices 31 and 32 of the humidity detection section 30 are electrically connected to the pad 40 through a wire 37. According to the embodiment, an end portion of the wire 37 on the far side from the humidity detection section 30 is exposed through an opening of the protection film 36 and serves as the pad 40.

As shown in FIG. 2, the detection electrode 33a of the detection capacitive device 31 is electrically connected to a pad 40a through a wire 37a. The detection electrode 33b of the detection capacitive device 31 and the reference electrode 34b of the reference capacitive device 32 are electrically connected to a pad 40b through a common wire 37b. The reference electrode 34a of the reference capacitive device 32 is electrically connected to a pad 40c through a wire 37c.

These wires 37a-37c are formed on the first surface 20a of the substrate 20, i.e., on the same plane as the detection electrodes 33a, 33b and the reference electrodes 34a, 34b. Further, like the detection electrodes 33a, 33b and the reference electrodes 34a, 34b, the wires 37a-37c are made from aluminum and covered with the protection film 36.

According to the embodiment, the pad 40 further includes a pad 40d which is electrically connected to the diffusion layer 21. A wire 37d extending along an edge of the substrate 20 having a rectangular planar shape is connected to the pad 40d. As shown in FIG. 3, a portion of the wire 37d is exposed through the opening of the protection film 36 and serves as the pad 40d. The wire 37d is formed on the first surface 20a of the substrate 20, i.e., on the same plane as the detection electrodes 33a, 33b and the reference electrodes 34a, 34b. Further, like the detection electrodes 33a, 33b and the reference electrodes 34a, 34b, the wire 37d is made from aluminum and covered with the protection film 36. As shown in FIG. 3, a contact hole 22a of the insulating layer 22 is filled with the wire 37d so that the wire 37d can be electrically connected to the diffusion layer 21. Therefore, when a constant potential (e.g., ground potential) is applied to the wire 37d through the pad 40d, the diffusion layer 21 can function as a shield layer against electromagnetic waves.

The pad 40 (40a-40d) is covered with the protection gel 60 under the condition where the bonding wire 115 is connected to the pad 40. The protection gel 60 protects the pad 40 made from aluminum from corrosion due to water and is made from water resistant material such as fluorinated gel. The protection gel 60 is applied around the pad 40 by using a dispenser or the like and then hardened.

Therefore, the protection gel 60 has flowability yet when the protection gel 60 is applied. If the protection gel 60, which is applied near the pad 40, flows toward the humidity detection section 30 and reaches the humidity-sensitive film 35 (35a, 35b), a propensity of the humidity-sensitive film 35 may be changed so that detection accuracy at ambient humidity may be reduced. For this reason, the dam section 50 is formed on the first surface 20a of the substrate 20 between the humidity detection section 30 and the pad 40. The dam section 50 prevents the protection gel 60, which is applied near the pad 40, from flowing toward the humidity detection section 30 and reaching the humidity-sensitive film 35.

The dam section 50 is made from the same material as the humidity-sensitive film 35 (35a, 35b) and therefore can be formed in the same process as the humidity-sensitive film 35 (35a, 35b). As shown in FIG. 2, according to the embodiment, the humidity detection section 30 is formed along one side of the rectangular planar shape of the first surface 20a of the substrate 20, and the pad 40 is formed along the other side of the rectangular planar shape. The dam section 50 is formed on the first surface 20a of the substrate 20 and extends from one to the other of opposing sides of the substrate 20 to separate a region where the humidity detection section 30 is formed from a region where the pad 40 is formed. The dam section 50 has almost the same thickness as the humidity-sensitive film 35.

Next, an example of a method of manufacturing the capacitive humidity sensor 10 is described.

First, a silicon wafer as the substrate 20 is prepared, and a silicon oxide layer is formed on a surface by thermal oxidation. Then, the diffusion layer 21 is formed by ion implantation of impurities into the surface of the substrate 20 through the silicon oxide layer. Then, the BPSG layer is formed on the silicon oxide layer so that the BPSG layer and the silicon oxide layer can become the insulating layer 22. Then, after the contact hole 22a is formed at a predetermined position of the insulating layer 22, aluminum is deposited all over the first surface 20a of the substrate 20. Then, the electrodes 33a, 33b, 34a, 34b, and the wire 37 (37a-37d) including the pad 40 (40a-40d) are formed by patterning. In this way, the electrodes 33a, 33b, 34a, and 34b of the humidity detection section 30 are formed on the same surface in the same process by using the same material.

Then, a silicon nitride layer as the protection film 36 is formed all over the first surface 20a of the substrate 20, and the pad 40 (40a-40d) is exposed by patterning. Then, after precursor is coated on the first surface 20a of the substrate 20, for example, by a spin coating method, a hardening treatment is performed. Then, the humidity-sensitive film 35 (35a, 35b) and the dam section 50 are formed by patterning. In this way, the humidity-sensitive film 35 of the humidity detection section 30 and the dam section 50 are formed in the same process by using the same material.

Then, the substrate 20 is diced into chips. Thus, the capacitive humidity sensor 10 can be manufactured. The manufactured capacitive humidity sensor 10 is mounted on the island 111, which is integrally formed with the casing 110, and connected to the circuit chip 113, which is mounded on the island 112, by the bonding wire 115. Then, the protection gel 60 is applied around the pad 40 by using a dispenser or the like so that the bonding wire 115 can be covered with the protection gel 60. Then, the protection gel 60 is hardened. Thus, the humidity detection apparatus 100 can be manufactured.

Next, the capacitive devices 31, 32 and a processing circuit of the capacitive humidity sensor 10 are described.

Figure 6:
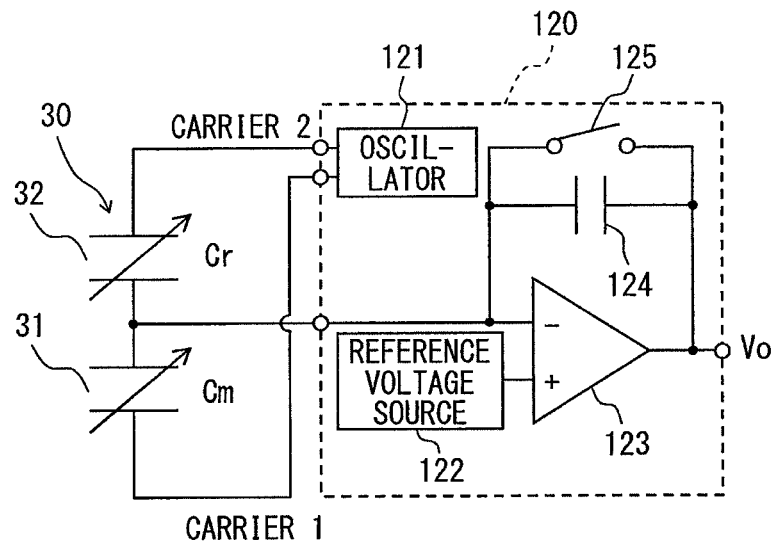
FIG. 6 is a diagram illustrating an example of an equivalent circuit of a capacitive device of the capacitive humidity sensor and a processing circuit of a circuit chip.

As shown in FIG. 6, the detection capacitive device 31 having the capacitance (a capacitance Cm) changing with the ambient relative humidity is connected in series with the reference capacitive device 32 having the capacitance (a capacitance Cr) changing with the ambient relative humidity. The circuit chip 113 includes a SC (switched capacitor) circuit 120 for converting a difference in capacitance between the capacitive devices 31, 32 to a voltage.

For example, as shown in FIG. 6, the SC circuit 120 includes an oscillator 121, a reference voltage source 122, a differential amplifier 123, a capacitor 124, an analog switch 125, and a sample-and-hold circuit (not shown). The oscillator 121 applies a carrier 1 and a carrier 2 to the capacitance Cm and the capacitance Cr, respectively. For example, the carriers 1 and 2 are rectangular waves, have the same amplitude of 5V, and have a phase difference of 180 degrees. For example, the reference voltage source 122 outputs a bias voltage of 2.5V. The differential amplifier 123 amplifies a difference between the bias voltage and a midpoint voltage between the capacitances Cm and Cr. The capacitor 124 has a predetermined capacitance.

Figure 7:
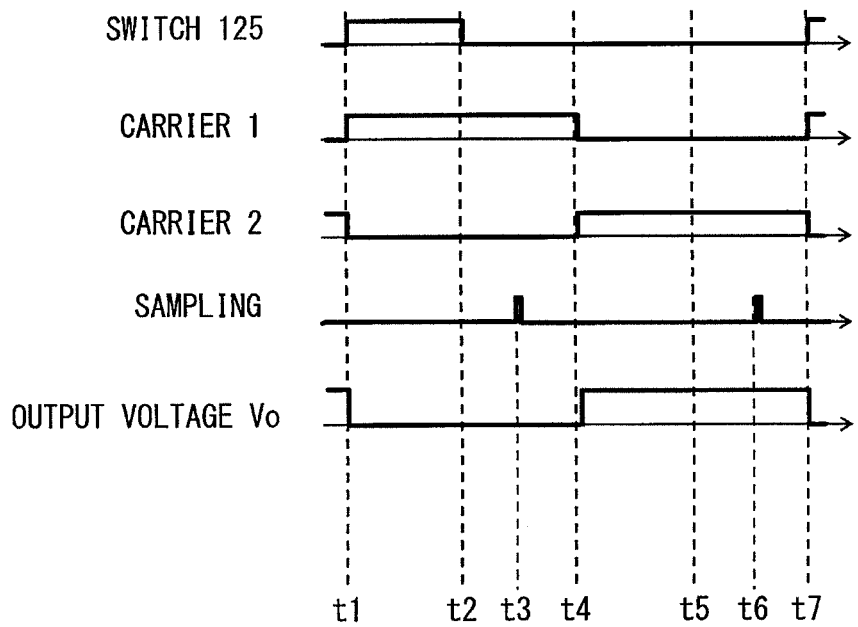
FIG. 7 is a timing diagram illustrating an example of a CV conversion action.

FIG. 7 is a timing chart showing an example of a CV conversion performed by the SC circuit 120. In the CV conversion performed by the SC circuit 120, as shown in FIG. 7, "reset->sample-and-hold->carrier switch->sample-and hold" is repeated as one cycle.

For example, when the analog switch 125 is turned ON at a time t1, the capacitor 124 is discharged (reset). Further, at the same time as the capacitor 124 is discharged, the carrier 1 rises, and the carrier 2 falls. At this time, the capacitances Cm and Cr are charged according to a relationship Cm>Cr and according to voltages respectively applied to the detection electrode 33a (refer to FIG. 2) of the capacitance Cm on the oscillator 121 side and the reference electrode 34b (refer to FIG. 2) of the capacitance Cr on the oscillator 121 side. By the way, the detection electrode 33b of the capacitance Cm and the reference electrode 34a of the capacitance Cr on the differential amplifier 123 side are changed to have a lot of negative charges.

Then, for example, when the analog switch 125 is turned OFF at a time t2, a closed loop circuit is constructed with the electrode 33b, the electrode 34a, and a terminal of the capacitor 124 on an inverting-input terminal side of the differential amplifier 123, so that the amount of charge stored from the time t1 to the time t2 can be maintained. For example, at a time t3 under this condition, an output voltage Vo of the SC circuit 120 is sampled and temporarily stored in an appropriate memory means.

Next, for example, at a time t4, the carrier 2 rises at the same time as the carrier 1 falls. When the carriers are inverted in this way, the electrodes 33b and 34a are changed to have a lot of positive charges. However, as described above, since the closed loop circuit is constructed with the electrode 33b, the electrode 34a, and the terminal of the capacitor 124 on the inverting-input terminal side of the differential amplifier 123, the amount of charge in the closed loop circuit is maintained. Therefore, the negative charges overflowing from the equilibrium of charge between the electrodes 33b and 34a moves to the terminal of the capacitor 124 on the inverting-input terminal side of the differential amplifier 123. As a result of this movement of charge, positive charges are stored in a terminal of the capacitor 124 on an output terminal side of the differential amplifier 123. Therefore, from a relationship "the amount of stored charge=capacitance×voltage", the output voltage Vo of the SC circuit 120 varies in proportion to the amount of moved charge and in inverse proportion to the capacitance of the capacitor 124.

The output voltage Vo varying as described above is outputted from an output terminal of the SC circuit 120. Then, for example, at a time t6, when the movement of charge is stopped, and a steady state arrives, the output voltage Vo is sampled and temporarily stored in an appropriate memory means. Then, a next cycle starts at a time t7 in the same way.

Ultimately, the ambient relative humidity is detected based on a value calculated by subtracting the voltage sampled at the time t3 from the voltage sampled at t6.

As described above, the difference in capacitance between the detection capacitive device 31 and the reference capacitive device 32 of the capacitive humidity sensor 10 is converted to the voltage by the CV conversion circuit (SC circuit 120), and the ambient relative humidity is detected based on the voltage. As the difference between the ratio of the detection capacitive device 31 (a capacitance Cm) and the ratio of the reference capacitive device 32 (a capacitance Cr) shown in FIG. 4 is larger, the change in the capacitance difference with respect to the change in the ambient humidity becomes larger. That is, the sensitivity of the capacitive humidity sensor 10 can be increased.

Next, the electrode gaps dm and dr, which are capable of reducing the size and improving the sensitivity of the capacitive humidity sensor 10, are described.

According to the embodiment, the reference capacitive device 32 is also provided with the humidity-sensitive film 35 (the reference humidity-sensitive film 35b), and the capacitance of the reference capacitive device 32 changes with the relative humidity. Therefore, the sensitivity of the capacitive humidity sensor 10 is lower compared to when the reference capacitive device 32 has no humidity-sensitive film 35. Therefore, in view of the sensitivity, it is preferable that the ratio of the reference capacitive device 32, i.e., a ratio C2/C1 of a capacitance C1 at the relative humidity of 0% (hereinafter referred to as the "0% RH") to a capacitance C2 at the relative humidity of 100% (hereinafter referred to as the "100% RH") be as small (close to 1) as possible. The sensitivity may be improved by increasing the ratio of the detection capacitive device 31 (a capacitance ratio C2/C1). However, in this case, since the size of the detection capacitive device 31 is increased, the size of the capacitive humidity sensor 10 is increased accordingly.

The ratio of the detection capacitive device 31, i.e., the ratio C2/C1 can be expressed by the following equation.

$$C2/C1 = (\in 2 \cdot \in 0 \cdot Sm/dm)/(\in 1 \cdot \in 0 \cdot Sm/dm) = \in 2/\in 1 \quad \text{(Equation 1)}$$

$\in 0$ represents a vacuum permittivity, $\in 1$ represents a relative permittivity at 0% RH of a dielectric of the detection capacitive device 31, $\in 2$ represents a relative permittivity at 100% RH of the dielectric, and Sm represents the overlapping area of the detection electrodes 33a, 33b.

The ratio of the reference capacitive device 32, i.e., the ratio C2/C1 can be expressed by the following equation.

$$C2/C1=(\epsilon 4 \cdot \epsilon 0 \cdot Sr/dr)/(\epsilon 3 \cdot \epsilon 0 \cdot Sr/dr)=\epsilon 4/\epsilon 3 \quad \text{(Equation 2)}$$

∈3 represents a relative permittivity at 0% RH of a dielectric of the reference capacitive device 32, ∈4 represents a relative permittivity at 100% RH of the dielectric, and Sr represents the overlapping area of the reference electrodes 34a, 34b.

In this way, the ratio of the detection capacitive device 31 is determined by ∈2/∈1, and the ratio of the reference capacitive device 32 is determined by ∈4/∈3. As mentioned previously, according to the embodiment, the detection humidity-sensitive film 35a and the reference humidity-sensitive film 35b are made from the same material and have the same thickness. Further, the detection electrodes 33a, 33b and the reference electrodes 34a, 34b are made from the same material and have the same width and thickness. In the equations 1 and 2, therefore, ∈1=∈3, and ∈2=∈4. Accordingly, the detection capacitive device 31 and the reference capacitive device 32 have a common (the same) relationship between the ratio (a capacitance ratio C2/C1) and the electrode gap. Therefore, which ratio is larger or smaller depends on the electrode gaps dm and dr.

Figure 8:
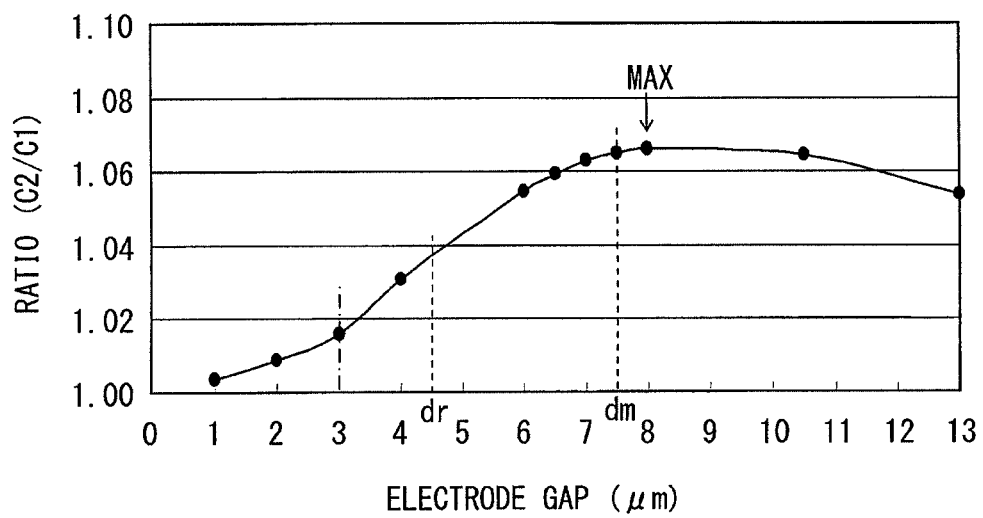
FIG. 8 is a diagram illustrating a relationship between an electrode gap and a ratio of a change in capacitance to a change in humidity (a capacitance ratio C2/C1)

FIG. 8 shows a result of a simulation conducted by the present inventors to evaluate the relationship between the electrode gap and the ratio (a capacitance ratio C2/C1). This simulation was conducted under conditions that the substrate 20 is made from silicon and has a thickness of 400 µm, the insulating layer 22 is made from silicon dioxide and has a thickness of 0.525 µm±0.0525 µm, the pairs of electrodes are made from aluminum and have a thickness of 0.7 µm±0.07 µm and a width of 4 µm±0.4 µm, the protection film 36 is made from silicon nitride and has a thickness of 1.6 µm±0.16 µm, the humidity-sensitive film 35 is made from polyimide, has a thickness of 2 µm±0.2 µm, and has a relative permittivity of 2.8 at 0% RH and 3.2 at 100% RH.

Figure 9:
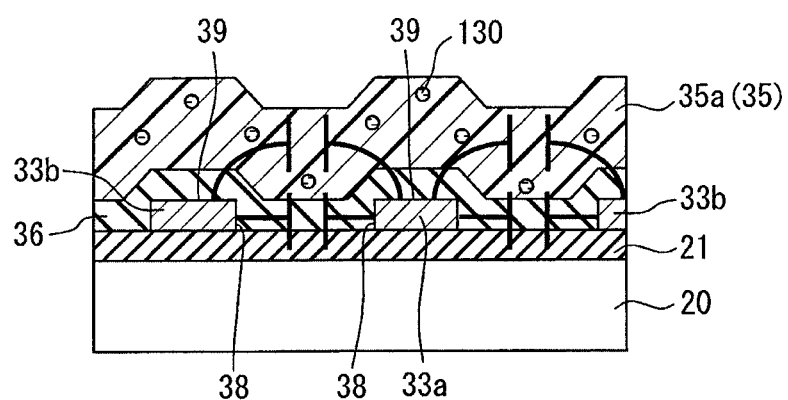
FIG. 9 is a diagram for explaining an overlap capacitance and an overlap capacitance.

As shown in FIG. 8, the ratio (a capacitance ratio C2/C1) peaks when the electrode gap is equal to 8 µm, increases with an increase in the electrode gap when the electrode gap is not greater than 8 µm, and decreases with the increase in the electrode gap when the electrode gap is greater than 8 µm. A reason why the relationship between the electrode gap and the ratio shows such a trend can be considered as follows. FIG. 9 is a cross-sectional diagram for explaining a capacitance constructed with an overlap capacitance and a fringe capacitance and illustrates the detection capacitive device 31 (a capacitance Cm), out of the capacitive devices 31 and 32, as an example. For the sake of expediency, the fringe capacitance of only an upper surface 39 side is illustrated.

The relative permittivity of the humidity-sensitive film 35 (a detection humidity-sensitive film 35a) itself does not change with the relative humidity. As shown in FIG. 9, however, depending on the amount of absorbed water 130, the relative permittivity of the whole, including the water 130, changes. Therefore, as the influence of the humidity-sensitive film 35 (35a) on the capacitance Cm formed between the detection electrodes 33a, 33b is larger, the ratio of the change in capacitance to the change in humidity becomes larger. As shown in FIG. 9, the capacitance of the detection capacitive device 31 depends on an overlap capacitance and a fringe capacitance in the pairs of opposing electrodes 33a and 33b. The overlap capacitance is formed between overlap surfaces 38. The fringe capacitance is formed between lower surfaces facing the substrate 20 and formed between upper surfaces 39 opposite to the lower surfaces.

As shown in FIG. 9, out of these capacitance components, in particular, the fringe capacitance formed between the upper surfaces 39 is generally much influenced by the humidity-sensitive film 35 (35a) when the thickness of the detection electrodes 33a and 33b (the height of the overlap surface 38) is greater than the width of the detection electrodes 33a and 33b (the length of the upper surface 39) because the humidity-sensitive film 35 (35a) located between the upper surfaces 39 is larger. Therefore, as a capacitance, the effect of the fringe capacitance is larger, and the ratio (a capacitance ratio C2/C1) becomes large. The reason why the ratio increases with the increase in the electrode gap dm until the electrode gap dm reaches the predetermined value of 8 µm can be considered that as the electrode gap dm is smaller, the influence of the overlap capacitance is larger (in other words, the influence of the humidity-sensitive film 35 is smaller) and that as the electrode gap dm is larger, the influence of the fringe capacitance is larger (in other words, the influence of the humidity-sensitive film 35 is larger). Further, the reason why the ratio decreases when the electrode gap dm exceeds the predetermined value of 8 µm can be considered that the fringe capacitance is less likely to be formed due to the wider electrode gap dm. The same is true for the reference capacitive device 32 (a capacitance Cr).

According to the embodiment, the electrode gap dr of the reference capacitive device 32 is set smaller than the electrode gap dm of the detection capacitive device 31 and the predetermined value of 8 µm at which the capacitance ratio C2/C1 peaks, and the electrode gas dm and dr are set so that the capacitance ratio C2/C1 of the detection capacitive device 31 is larger than that of the reference capacitive device 32. Specifically, each of the electrode gaps dm and dr is smaller than the predetermined value of 8 µm at which the capacitance ratio C2/C1 peaks. Further, the electrode gap dr of the reference capacitive device 32 is set smaller than the electrode gap dm of the detection capacitive device 31. Specifically, the electrode gap dm of the detection capacitive device 31 is set so that the influence of the fringe capacitance is large, more specifically, set to 7.5 µm. Therefore, the ratio of the detection capacitive device 31 is about 1.065. On the other hand, the electrode gap dr of the reference capacitive device 32 is set so that the influence of the fringe capacitance is small. Therefore, the ratio of the reference capacitive device 32 is about 1.035.

As described above, the electrode gaps dm and dr are set so that the capacitance ratio C2/C1 of the detection capacitive device 31 can be larger than that of the reference capacitive device 32. Therefore, the sensitivity of the capacitive humidity sensor 10 is improved.

Further, within a range where the capacitance ratio C2/C1 of the detection capacitive device 31 is larger than that of the reference capacitive device 32, the electrode gap dr of the reference capacitive device 32 is set smaller than both the electrode gap dm of the detection capacitive device 31 and the predetermined value at which the capacitance ratio C2/C1 peaks. That is, the electrode gap dr of the reference capacitive device 32 is set so that the influence of the fringe capacitance is small. Thus, the size of the reference capacitive device 32 and therefore the size of the capacitive humidity sensor 10 can be reduced.

As described above, according to the embodiment, it is possible to improve the sensitivity and to reduce the size of the capacitive humidity sensor 10 in which the detection capacitive device 31 and the reference capacitive device 32 with the humidity-sensitive film 35 (the reference humidity-sensitive film 35*b*) are formed on the same surface 20*a* of the substrate 20.

In particular, according to the embodiment, the electrode gap dm of the detection capacitive device 31 is not greater than the predetermined value at which the capacitance ratio C2/C1 peaks. Thus, as described above, it is possible to improve the sensitivity and to reduce the size of the detection capacitive device 31 and therefore the size of the capacitive humidity sensor 10.

As mentioned previously, when the electrode gap exceeds the predetermined value (8 μm in FIG. 8) at which the ratio peaks, the ratio decreases with the increase in the electrode gap. Therefore, when the electrode gap dr of the reference capacitive device 32 is set greater than the electrode gap dm of the detection capacitive device 31 within a range where the electrode gap exceeds the predetermined value at which the capacitance ratio C2/C1 peaks, the difference in the ratio between the detection capacitive device 31 and the reference capacitive device 32 is increased so that the sensitivity can be improved. However, in this case, the electrode gap dr of the reference capacitive device 32 needs to be increased accordingly. Therefore, it is difficult to reduce the size of the reference capacitive device 32 and therefore the size of the capacitive humidity sensor 10.

Further, according to the embodiment, the protection film 36 covers the electrodes 33*a*, 33*b*, 34*a*, and 34*b* to protect the electrodes 33*a*, 33*b*, 34*a*, and 34*b* from corrosion due to water. Thus, the reference electrodes 34*a* and 34*b* can be effectively protected from the corrosion by the reference humidity-sensitive film 35 and the protection film 36. Likewise, the detection electrodes 33*a* and 33*b* can be effectively protected from the corrosion. Further, the detection humidity-sensitive film 35*a* and the reference humidity-sensitive film 35*b* are formed on the protection film 36. Thus, a dielectric of the overlap capacitance is provided mainly by the protection film 36, and a dielectric of the fringe capacitance between the upper surfaces 39 is provided mainly by the humidity-sensitive film 35. Therefore, the change in the ratio (a capacitance ratio C2/C1) by the electrode gap can be large compared to when the humidity-sensitive film 35 (35*a*, 35*b*) is in contact with the electrodes 33*a*, 33*b*, 34*a*, and 34*b* without the protection film 36. Accordingly, the difference in the ratio between the detection capacitive device 31 and the reference capacitive device 32 can be increased.

Figure 10A:
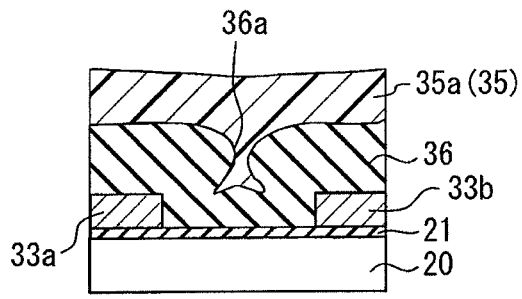
FIG. 10A is a diagram illustrating a cross-sectional view to show a relationship between the electrode gap and a shape of a valley portion of a protection film when the electrode gap is 1.5 μm.
Figure 11:
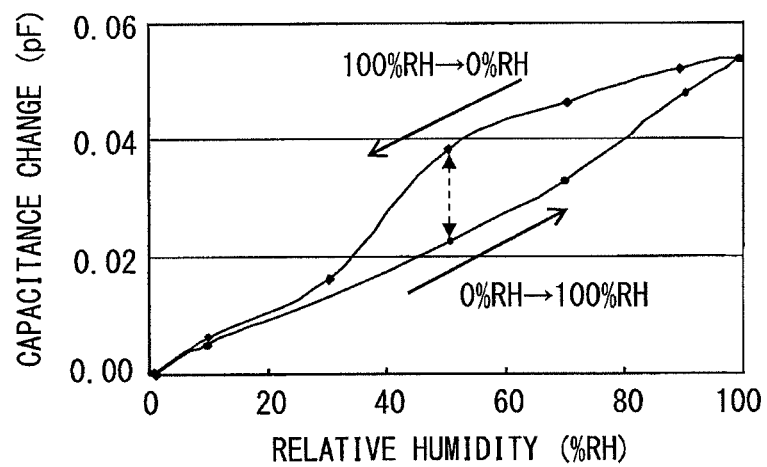
FIG. 11 is a diagram illustrating a relationship between a capacitance change and a degree of hysteresis when the electrode gap is 1.5 μm.
Figure 12:
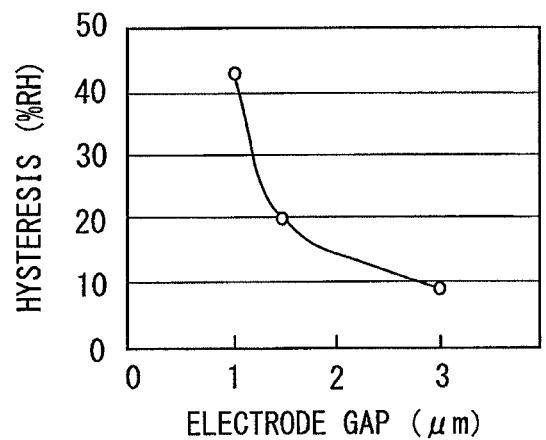
FIG. 12 is a diagram illustrating a relationship between the electrode gap and the degree of hysteresis.

By the way, as shown in FIG. 10A, if the electrode gap dm is small, an opening width of a valley portion 36*a* of the protection film 36, which is created depending on the gap between the detection electrodes 33*a* and 33*b*, becomes small. FIG. 10A shows a cross-sectional structure observed by a SEM when the electrode gap dm is 1.5 μm. If the opening width of the valley portion 36*a* is small, the water absorbed by the humidity-sensitive film 35 (the detection humidity-sensitive film 35*a*) located in the valley portion 36*a* is less likely to evaporate. Therefore, as shown in FIG. 11, there arises a difference in the capacitance change with respect to the relative humidity between when the relative humidity increases and when the relative humidity decreases, i.e., hysteresis occurs. It is noted that FIG. 11 shows a case where the electrode gap dm is 1.5 μm. As shown in FIG. 12, the magnitude of hysteresis indicated by a broken arrow in FIG. 11 is equivalent to 20% of the relative humidity change.

As shown in FIG. 12, when the electrode gap dm is smaller and equal to 1.0 μm, the magnitude of hysteresis is equivalent to 43% of the relative humidity change.

Figure 10B:
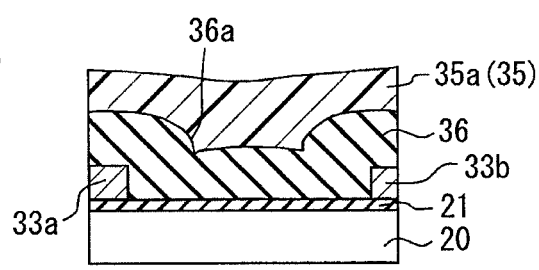
FIG. 10B is a diagram illustrating a cross-sectional view to show a relationship between the electrode gap and the shape of the valley portion of the protection film when the electrode gap is 3.0 μm.

On the other hand, as shown in FIG. 10B, if the electrode gap dm is large, the opening width of the valley portion 36*a* of the protection film 36, which is created depending on the gap between the detection electrodes 33*a* and 33*b*, becomes large. FIG. 10B shows a cross-sectional structure observed by the SEM when the electrode gap dm is 3.0 μm. If the opening width of the valley portion 36*a* is large, the water absorbed by the humidity-sensitive film 35 (the detection humidity-sensitive film 35*a*) located in the valley portion 36*a* is likely to evaporate so that the hysteresis can be reduced. As shown in FIG. 12, when the electrode gap dm is 3.0 μm, the magnitude of hysteresis is equivalent to 9% of the relative humidity change. Although the above description relates to the electrode gap dm, the same is true for the electrode gap dr.

According to the embodiment, each of the electrode gap dr of the reference capacitive device 32 and the electrode gap dm of the detection capacitive device 31 is not less than the sum of the thickness of the protection film 36 and the thickness of the electrodes 33*a*, 33*b*, 34*a*, and 34*b*. As shown in the parameters of the simulation, according to the embodiment, the pairs of electrodes have the thickness of 0.7 μm±0.07 μm, and the protection film 36 has the thickness of 1.6 μm±0.16 μm. The electrode gaps dm and dr are set so that the electrode gaps dm and dr can be not less than 3 μm (a chain line in FIG. 8) which is calculated by adding a margin to 2.57 μm which is the maximum value of the sum of the thicknesses. In such an approach, as shown in FIG. 10B, the opening width of the valley portion 36*a* of the protection film 36, which is created depending on the gap between the electrodes, can become large enough to allow the water absorbed by the humidity-sensitive film 35 (35*a*, 35*b*) located in the valley portion 36*a* to evaporate. Thus, the hysteresis can be reduced.

Further, according to the embodiment, the detection electrodes 33*a* and 33*b* have a comb-shape, and the reference electrodes 34*a* and 34*b* have a comb-shape. In such an approach, each of the overlapping area of the pair of the detection electrodes 33*a* and 33*b* and the overlapping area of the pair of the reference electrodes 34*a* and 34*b* is increased. Thus, the sensitivity of the capacitive humidity sensor 10 can be increased while reducing the increase in the size.

Further, according to the embodiment, the detection humidity-sensitive film 35*a* and the reference humidity-sensitive film 35*b* are integrated as single humidity-sensitive film 35. Thus, the structure can be simplified. In addition, the contact area between the humidity-sensitive film 35 and the substrate 20 is increased. Therefore, the humidity-sensitive film is less likely to be detached compared to when the detection humidity-sensitive film 35*a* and the reference humidity-sensitive film 35*b* are separate pieces. In particular, the detachment can be reduced during a dicing process.

(Modification)

In the embodiment, the electrode gap dm of the detection capacitive device 31 is different from the predetermined value at which the capacitance ratio C2/C1 peaks. However, more preferably, the electrode gap dm can be equal to the predetermined value (8 μm in FIG. 8) at which the capacitance ratio C2/C1 peaks. In such an approach, the ratio of the detection capacitive device 31 is maximized so that the difference in the ratio between the detection capacitive device 31 and the reference capacitive device 32 can be further increased. Accordingly, the sensitivity of the capacitive humidity sensor 10 can be further increased.

Likewise, the electrode gap dr of the reference capacitive device 32 is not limited to 4.5 μm. For example, the electrode gap dr can be not greater than half of the predetermined value at which the capacitance ratio C2/C1 peaks.

In such an approach, the ratio of the reference capacitive device 32 is further reduced (becomes much closer to 1), so that the sensitivity can be increased. In the example of FIG. 8, the electrode gap dr can be not greater than 4 μm. The difference in the ratio between the detection capacitive device 31 and the reference capacitive device 32 can be further increased by making the electrode gap dr as small as possible within a range where the hysteresis is reduced. Accordingly, the sensitivity of the capacitive humidity sensor 10 can be further increased. For example, the sensitivity can be further increased by reducing the electrode gap dr from 4.5 μm to 3 μm.

While the present disclosure has been described with reference to embodiments thereof, it is to be understood that the disclosure is not limited to the embodiments. The present disclosure is intended to cover various modifications and equivalent arrangements within the spirit and scope of the present disclosure.

The number of the detection electrodes 33a and 33b is not limited to the embodiment. It is only necessary that at least one detection electrode 33a and at least one detection electrode 33b are paired. Likewise, it is only necessary that at least one reference electrode 34a and at least one reference electrode 34b are paired.

It is only necessary that the electrode gap dr of the reference capacitive device 32 is set smaller than the electrode gap dm of the detection capacitive device 31 and the predetermined value at which the capacitance ratio C2/C1 peaks, and the electrode gas dm and dr are set so that the capacitance ratio C2/C1 of the detection capacitive device 31 is larger than that of the reference capacitive device 32. Therefore, unlike in the embodiment, the electrode gap dm can be set greater than the predetermined value at which the capacitance ratio C2/C1 peaks. Further, the electrode gaps dm and dr can be smaller than 3 μm. Furthermore, each of the electrodes gap dm and dr is not less than the sum of the thickness of the protection film 36 and the thickness of the electrodes 33a, 33b, 34a, and 34b.

According to the embodiment, the substrate 20 of the capacitive humidity sensor 10 has the diffusion layer 21, the wire 37d, and the pad 40d electrically connected to the diffusion layer 21. It is not always necessary that the substrate 20 has these structures.

According to the embodiment, the circuit chip 113 is configured as a separate chip from the capacitive humidity sensor 10. Alternatively, a processing circuit of the circuit chip 113 can be integrated in the substrate 20 of the capacitive humidity sensor 10 as a single chip.

According to the embodiment, the detection humidity-sensitive film 35a and the reference humidity-sensitive film 35b are integrated as a single humidity-sensitive film 35. Alternatively, the detection humidity-sensitive film 35a and the reference humidity-sensitive film 35b can be separate films.

According to the embodiment, the protection film 36 is located on the electrodes 33a, 33b, 34a, and 34b, and the humidity-sensitive film 35 (35a, 35b) is located on the protection film 36. Alternatively, the humidity-sensitive film 35 (35a, 35b) can be directly located on the electrodes 33a, 33b, 34a, and 34b without the protection film 36.

According to the embodiment, the dam section 50 is made from the same material as the humidity-sensitive film 35. The structure of the dam section 50 is not limited to the embodiment. Also, the dam section 50 is not always necessary.

What is claimed is:

1. A capacitive humidity sensor comprising:
a substrate;
a detection capacitive device formed in the substrate and having a capacitance changing at a first ratio with respect to a change in ambient humidity; and
a reference capacitive device formed in the substrate and having a capacitance changing at a second ratio smaller than the first ratio with respect to the change in ambient humidity, wherein
the detection capacitive device includes a pair of detection electrodes and a detection humidity-sensitive film,
the detection electrodes face each other on a predetermined mounting surface of the substrate and are spaced from each other by a first gap,
the detection humidity-sensitive film covers the detection electrodes and has a relative permittivity changing with absorption of water,
the reference capacitive device includes a pair of reference electrodes and a reference humidity-sensitive film,
the reference electrodes face each other on the mounting surface of the substrate and are spaced from each other by a second gap,
the reference humidity-sensitive film covers the reference electrodes and has a relative permittivity changing with absorption of water,
the detection humidity-sensitive film and the reference humidity-sensitive film are made of the same material and have the same thickness,
the detection electrodes and the reference electrodes are made of the same material and have the same width and thickness,
the first ratio is a ratio of the capacitance of the detection capacitive device at a relative humidity of 100% to the capacitance of the detection capacitive device at the relative humidity of 0%,
the second ratio is a ratio of the capacitance of the reference capacitive device at the relative humidity of 100% to the capacitance of the reference capacitive device at the relative humidity of 0%,
a relationship between the first ratio and the first gap is the same as a relationship between the second ratio and the second gap,
a value of the first ratio peaks when the first gap is equal to a first predetermined width,
the value of the first ratio increases with an increase in width of the first gap when the first gap is smaller than the first predetermined width,
the value of the first ratio decreases with an increase in width of the first gap when the first gap is larger than the first predetermined width,
a value of the second ratio peaks when the second gap is equal to a second predetermined width,
the value of the second ratio increases with an increase in width of the second gap when the second gap is smaller than the second predetermined width,
the value of the second ratio decreases with an increase in width of the second gap when the second gap is larger than the second predetermined width,
the first predetermined width is equal to the second predetermined width, and
the second gap is smaller than the first gap and the second predetermined width.

2. The capacitive humidity sensor according to claim 1, wherein the first gap is not greater than the first predetermined width.

3. The capacitive humidity sensor according to claim 2, wherein the first gap is equal to the first predetermined width.

4. The capacitive humidity sensor according to claim 1, further comprising:

a protection film that covers each electrode to protect each electrode from corrosion due to water, wherein the detection humidity-sensitive film and the reference humidity-sensitive film are formed on the protection film, and the first predetermined width is 8 μm.

5. The capacitive humidity sensor according to claim 4, wherein a width of the first gap is not smaller than the sum of a thickness of the protection film and the thicknesses of the detection electrodes, a width of the second gap is not smaller than the sum of a thickness of the protection film and thicknesses of the reference electrodes, and widths of the first gap and the second gap range from 3 μm to 8 μm inclusive.

6. The capacitive humidity sensor according to claim 1, wherein each of the detection electrodes and the reference electrodes has a comb-shape.

7. The capacitive humidity sensor according to claim 1, wherein the detection humidity-sensitive film and the reference humidity-sensitive film are integrated as a single humidity-sensitive film.

8. The capacitive humidity sensor according to claim 1, wherein the capacitance of the detection capacitive device includes an overlap capacitance which is formed between opposing surfaces of the pair of detection electrodes, and a fringe capacitance which is formed between upper surfaces of the pair of detection electrodes and formed between lower surfaces of the pair of detection electrodes;

the capacitance of the reference capacitive device includes an overlap capacitance which is formed between opposing surfaces of the pair of reference electrodes, and a fringe capacitance which is formed between upper surfaces of the pair of reference electrodes and formed between lower surfaces of the pair of reference electrodes; and the capacitive humidity sensor has a construction including:

the first gap being smaller than the first predetermined width, wherein the fringe capacitance of the detection capacitive device increases with an increase in width of the first gap and the overlap capacitance of the detection capacitive device decreases with an increase in width of the first gap, and the second gap being smaller than the second predetermined width, wherein fringe capacitance of the reference capacitive device increases with an increase in width of the second gap and the overlap capacitance of the reference capacitive device decreases with an increase in width of the second gap.

* * * * *